US007985587B2

(12) United States Patent
Morgan et al.

(10) Patent No.: US 7,985,587 B2
(45) Date of Patent: Jul. 26, 2011

(54) METHODS OF CULTURING DERMAL PAPILLA CELLS

(75) Inventors: Bruce A. Morgan, Lexington, MA (US); Jiro Kishimoto, Yokohama (JP); Robert Burgeson, Marblehead, MA (US)

(73) Assignee: The General Hospital Corporation, Boston, MA (US)

( * ) Notice: Subject to any disclaimer, the term of this patent is extended or adjusted under 35 U.S.C. 154(b) by 940 days.

(21) Appl. No.: 11/701,835

(22) Filed: Feb. 2, 2007

(65) Prior Publication Data
US 2008/0286261 A1 Nov. 20, 2008

Related U.S. Application Data

(60) Division of application No. 11/129,215, filed on May 13, 2005, now Pat. No. 7,175,842, which is a continuation of application No. 10/791,368, filed on Mar. 2, 2004, now abandoned, which is a division of application No. 09/822,722, filed on Mar. 30, 2001, now Pat. No. 6,924,141.

(60) Provisional application No. 60/261,690, filed on Jan. 12, 2001, provisional application No. 60/193,771, filed on Mar. 31, 2000.

(51) Int. Cl.
*C12N 5/00* (2006.01)

(52) U.S. Cl. ........ 435/371; 435/325; 435/352; 435/366; 435/375; 435/405

(58) Field of Classification Search ............ None
See application file for complete search history.

(56) References Cited

U.S. PATENT DOCUMENTS

| 5,091,173 | A | * | 2/1992 | Buultjens et al. ............ 514/3 |
| 5,208,145 | A |   | 5/1993 | Rogers |
| 5,686,289 | A |   | 11/1997 | Humes et al. |
| 6,159,950 | A |   | 12/2000 | Crystal et al. |
| 6,485,972 | B1 |   | 11/2002 | McMahon et al. |
| 7,067,474 | B1 |   | 6/2006 | Birchmeier et al. |

FOREIGN PATENT DOCUMENTS

| CA | 2357015 | 8/1999 |
| JP | 408066183 A | 3/1996 |
| WO | WO 95/17416 | 6/1995 |
| WO | WO 97/17982 | 5/1997 |
| WO | WO 99/42481 | 8/1999 |
| WO | WO 00/31134 | 6/2000 |

OTHER PUBLICATIONS

Chen et al., "Wnt Signaling to β-Catenin Involves Two Interactive Components," J. Biol. Chem., 275:17894-99 (2000).
Cross et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf," Biochem. J., 303:21-26 (1994).
Davies et al., "Specificity and mechanism of action of some commonly used protein kinase inhibitors," Biochem. J., 351:95-105 (2000).
Desbois-Mouthon et al., "Insulin and IGF-1 stimulate β-catenin pathway through two signalling cascades involving GSK-3β inhibition and Ras activation," Oncogene, 20:252-259 (2001).
Eldar-Finkelman et al., "Inactivation of Glycogen Synthase Kinase-3 by Epidermal Growth Factor Is Mediated by Mitogen-activated Protein Kinase/p90 Ribosomal Protein S6 Kinase Signaling Pathway in NIH/3T3 Cells," J. Biol. Chem., 270:987-990 (1995).
Fang et al, "Phosphorylation and inactivation of glycogen synthase kinase 3 by protein kinase A," Proc. Natl. Acad. Sci. USA, 97:11960-65 (2000).
Farr et al., "Interaction among GSK-3, GBP, Axin, and APC in Xenopus Axis Specification," J. Cell Biol., 148:691-701 (2000).
Frame et al., "GSK3 takes centre stage more than 20 years after its discovery," Biochem. J., 359:1-16 (2000).
Hedgepeth et al., "Regulation of Glycogen Synthase Kinase 3β and Downstream Wnt Signaling by Axin," Mol. Cell. Biol., 19:7147-57 (1999).
Klein et al., "A molecular mechanism for the effect of lithium on development," Proc. Natl. Acad. Sci. USA, 93:8455-59 (1996).
Leclerc et al., "Indirubins Inhibit Glycogen Synthase Kinase-3β and CDK5/P25, Two Protein Kinases Involved in Abnormal Tau Phosphorylation in Alzheimer's Disease," J. Biol. Chem., 276:251-260 (2001).
Leost et al., "Paullones are potent inhibitors of glycogen synthase kinase-3β and cyclin-depedent kinase 5/p25," Eur. J. Biochem., 267:5983-94 (2000).
Meijer et al., "Pharmacological inhibitors of glycogen synthase kinase 3," Trends Pharm. Sci., 25:1-10 (2004).
Moule et al., "Regulation of Protein Kinase B and Glycogen Synthase Kinase-3 by Insulin and β-Adrenergic Agonists in Rat Epididymal Fat Cells," J. Biol. Chem., 272:7713-19 (1997).
Saito et al., "The mechanism by which epidermal growth factor inhibits glycogen synthase kinase 3 in A431 cells," Biochem. J., 303:27-31 (1994).
Stambolic et al., "Mitogen inactivation of glycogen synthase kinase-3β in intact cells via serine 9 phosphorylation," Biochem. J., 303:701-704 (1994).
Sutherland et al., "Inactivation of glycogen synthase kinase-3β by phosphorylation: new kinase connections in insulin and growth-factor signaling," Biochem. J., 296:15-19 (1993).
Arias et al., "Wnt signaling: pathway or network?", Aug. 1999, Curr.Opin.Genet.Dev., vol. 9, No. 4;447-54.
Charpentier et al., "Plakoglobin Suppresses Epithelial Proliferation and Hair Growth In Vivo", Apr. 17, 2000, J. Cell Biol., vol. 149, No. 2;503-519.

(Continued)

*Primary Examiner* — Leon B Lankford
(74) *Attorney, Agent, or Firm* — Fish & Richardson P.C.

(57) ABSTRACT

The invention features methods of promoting hair growth in a subject. The methods include inducing or mimicking the effects of Wnt promoted signal transduction, e.g., by increasing the level of Wnt protein or administering an agent which mimics an effect of Wnt promoted signal transduction, e.g., by administering lithium chloride. Methods of inhibiting hair growth are also provided.

6 Claims, No Drawings

OTHER PUBLICATIONS

Christiansen et al., "Murine Wnt-11 and Wnt-12 have temorally . . . ", Jun. 1995, Mech.Dev., vol. 51, No. 2,3;341-50.

Chuong et al., "Early Events During Avian Skin Appendage Regeneration: . . . ", 1996, J. Invest. Dermatol., vol. 107;639-646.

DasGupta et al., "Multiple roles for activated LEF/TCF transcription complexes . . . ", Development, vol. 126, Oct. 1999;4557-4568.

Gat et al., "De Novo Hair Follicle Morphogenesis and Hair Tumors . . . ", Cell, vol. 95, Nov. 25, 1998;605-614.

Gavin et al., "Expression of mutiple novel Wnt-1/int-1-related . . . ", Dec. 1990, Genes Dev., vol. 4, No. 12b;2319-2332.

Genderen et al., "Development of several organs that require inductive epithial . . . ", Genes & Develpoment, vol. 8, No. 22, Nov. 15, 1994;2691-2703.

Goodrich et al., "Conservation of the hedgehog/patched . . . ", Feb. 1996, 90Genes Dev., vol. 10, No. 3;301-12.

Hardy, "The secret life of the hair follicle", 1992, Trends in Genetics, vol. 8;55-61.

Kengaku et al., "Distinct WNT pathways regulating AER . . . ", May 1998, Science, vol. 280;1274-1277.

Kishimoto et al., "Selective activation of the versican . . . ", Jun. 1999, Proc.Natl. Acad.Sci. USA, vol. 96, No. 13.

Kishimoto et al., "Wnt signaling maintains the hair-inducing activity of the dermal papilla", 2000, vol. 14;1181-1185.

Lee et al., "Insertional mutagenesis identifies a member of the Wnt . . . ", Mar. 1995, Proc.Natl.Acad.Sci. USA, vol. 92, No. 6;2268-2272.

Marigo et al., "Conservation in hedgehog signaling . . . ", Apr. 1996, Development, vol. 122, No. 4;1225-1233.

Millar et al., "WNT Signaling in the Control of Hair Growth and Structure", Development Biology, vol. 207, No. 1, Mar. 1, 1999;133-149.

Noramly et al., "β-catenin signaling can initiate feather bud development", Development, vol. 126, Aug. 1999;3509-3521.

Nusse et al., "Wnt Genes", Cell, vol. 69, Jun. 26, 1992;1073-1087.

Oro et al., "Splitting Hairs: Dissecting Roles of Sighnaling Systems in Epideraml Development", Cell, vol. 95, Nov. 25, 1998;575-578.

Pennisi, "Hairy Mice Offer Hope for Baldness Remedy", Science, vol. 282, Nov. 27, 1998; 1617-1619.

Riddle et al., "Induction of the LIM homeobox gene . . . ", Nov. 1995, Cell, vol. 83, No. 4;631-640.

Sato et al., "Induction of hair growth phase . . . ", Oct. 1999, J.Clin. Invest., vol. 104, No. 7;855-864.

St. Jacques et al., "Sonic hedgehog signaling . . . ", Sep. 1998, Curr.Biol., vol. 8, No. 19;1058-1068.

Veer et al., "Molecular cloning and chromosomal . . . ", Nov. 1984, Mol.Cell Biol., vol. 4, No. 11;2532-2534.

Wainwright et al., "Isolation of a human gene with protein sequence . . . ", 1988, vol. 7, No. 6;1743-1748.

International Search Report, Jul. 27, 2001.

\* cited by examiner

METHODS OF CULTURING DERMAL PAPILLA CELLS

RELATED APPLICATIONS

This application is a divisional of U.S. Ser. No. 11/129,215, filed May 13, 2005, now U.S. Pat. No. 7,175,842 which is a continuation of U.S. Ser. No. 10/791,368, filed Mar. 2, 2004, now abandoned which is a divisional of U.S. Ser. No. 09/822,722, filed Mar. 30, 2001, now U.S. Pat. No. 6,924,141, which claims the benefit of U.S. Provisional Application Ser. No. 60/261,690, filed Jan. 12, 2001, and U.S. Provisional Application Ser. No. 60/193,771, filed Mar. 31, 2000. The contents of all the preceding applications are incorporated herein by reference in their entirety.

BACKGROUND OF THE INVENTION

The hair follicle undergoes a cycle of hair growth (anagen) followed by regression (catagen), and quiescence (telogen) until a new hair shaft is generated in the existing follicle during the subsequent anagen phase. Hardy et al. (1992) Trends in Genetics 8:55-61. The hair shaft is derived from the epithelial matrix cells at the base of the follicle, but a cluster of dermal cells ensheathed by the matrix cells, known as the dermal papilla (DP), is thought to supply inductive signals required for hair outgrowth. Reciprocal signaling from the epidermis is required for the formation of the dermal papilla and may also explain the coordinated morphological changes in epithelial and dermal components of the follicle observed during the hair cycle.

SUMMARY OF THE INVENTION

The invention is based, in part, on the discovery that increasing Wnt protein levels can positively regulate the ability of dermal papilla (DP) cells to promote hair growth. It was found that co-culture of Wnt expressing cells with DP cells maintains hair inductivity. In addition, it was found that agents, such as inhibitors of GSK3β kinase, e.g., lithium chloride or similar small ions, which can mimic an effect of Wnt promoted signal transduction, e.g., inhibition of β-catenin phosphorylation, e.g., by inhibition of GSK3β kinase, or accumulation of β-catenin, can regulate the ability of DP cells to promoter hair growth.

Accordingly, in one aspect, the invention features a method of promoting hair growth in a subject. The method includes inducing or mimicking the effects of Wnt promoted signal transduction, e.g., by increasing the level of Wnt protein or administering an agent which mimics an effect of Wnt promoted signal transduction, e.g., inhibition of β-catenin phosphorylation, e.g., by inhibition of GSK3β kinase, or accumulation of β-catenin, to thereby promote hair growth.

In a preferred embodiment, the Wnt protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, Wnt is increased by administering an agent which increases the level of Wnt protein production and/or activity. An agent which increases the level of Wnt protein and/or which mimics an effect of Wnt promoted signal transduction can be one or more of: a Wnt polypeptide or a functional fragment or analog thereof; a nucleotide sequence encoding a Wnt polypeptide or functional fragment or analog thereof; an agent which increases Wnt nucleic acid expression, e.g., a small molecule which binds to the promoter region of Wnt; an agent which mimics an effect of Wnt promoted signal transduction, e.g., inhibition of β-catenin phosphorylation, e.g., by inhibition of GSK3β kinase, or accumulation of β-catenin. Examples of agents which can mimic an effect of Wnt promoted signal transduction include: an inhibitor of GSK3β kinase, e.g., lithium chloride or similar small ions; agents which bind Frizzled (Frz) (a cell surface receptor) and mimic Wnt binding, e.g., anti-Frizzled antibodies, or other naturally or non-naturally occurring Frizzled binding ligands.

In a preferred embodiment, Wnt is increased by administering, e.g., introducing, a nucleotide sequence encoding a Wnt polypeptide or functional fragment or analog thereof, into a particular cell, e.g., an epidermal cell or a DP cell, in the subject. The nucleotide sequence can be a genomic sequence or a cDNA sequence. The nucleotide sequence can include: a Wnt coding region; a promoter sequence, e.g., a promoter sequence from a Wnt gene or from another gene; an enhancer sequence, e.g., 5' untranslated region (UTR), e.g., a 5' UTR from a Wnt gene or from another gene, a 3' UTR, e.g., a 3' UTR from a Wnt gene or from another gene; a polyadenylation site; an insulator sequence.

In another preferred embodiment, the level of Wnt protein is increased by increasing the level of expression of an endogenous Wnt gene, e.g., by increasing transcription of the Wnt gene. In a preferred embodiment, transcription of the Wnt gene is increased by: altering the regulatory sequences of the endogenous Wnt gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Wnt gene to be transcribed more efficiently.

In another embodiment, the method can include introducing a cell into a subject, e.g., a cell expressing Wnt. In a preferred embodiment, the cell expresses a Wnt protein, e.g., a Wnt 3, Wnt 4, or Wnt 7, or a fragment or an analog thereof. In another preferred embodiment, the cell has been genetically modified to cause the expression of Wnt, e.g., the cell has been genetically modified to express a Wnt protein, or a fragment or an analog thereof, or the cell has been genetically modified to introduce a nucleic acid sequence, e.g., a regulatory sequence, e.g., a promoter or an enhancer, that causes or increases the expression of the endogenous Wnt. In a preferred embodiment, the promoter of the endogenous Wnt gene has been replaced by another promoter, e.g., by a promoter from another gene. The cell can be an autologous, allogeneic, or xenogeneic cell, but is preferably autologous. The autologous cell is preferably from a subject characterized with hair loss. The manipulated cell can be any cell type, e.g., a fibroblast, a keratinocyte, an epithelial cell, an endothelial cell, a glial cell, a neural cell, a lymphocyte, a bone marrow cell, and a muscle cell. Preferably the cell is an epithelial cell, e.g., an epidermal cell, a hair follicle cell, a dermal papilla cell. The cell can be introduced into a subject to increase Wnt activity.

In a preferred embodiment, the level of Wnt, e.g., Wnt 3, Wnt 4, or Wnt 7, is increased over a sustained period of time, e.g., a period equal to or greater than 2, 10, 14, 30, 60, 90, or 180 days. E.g., a cell expressing a Wnt protein, fragment, or analog can be supplied, e.g., by any method described herein, whereby Wnt is released over a sustained period of time, e.g., a period equal to or greater than 2, 10, 14, 30, 60, 90, or 180 days.

In a preferred embodiment, the agent which increases the level of Wnt protein or mimics an effect of Wnt promoted signal transduction is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the Wnt protein level or Wnt promoted signal transduction is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair growth is promoted on: the subject's scalp; the subject's face, e.g., beard and/or mustache facial hair growth is promoted.

In a preferred embodiment, the subject has an insufficient amount of hair or an insufficient rate of hair growth. In a preferred embodiment, the subject suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

In another aspect, the invention features a method of inhibiting hair growth in a subject. The method includes inhibiting the level of Wnt protein or inhibiting an effect of Wnt promoted signal transduction, in the subject.

In a preferred embodiment, the Wnt protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, Wnt is inhibited by administering an agent which inhibits Wnt protein production levels and/or is a Wnt antagonist. An agent which inhibits Wnt can be one or more of: a Frizzled protein or Wnt binding portion thereof; a Wnt nucleic acid molecule which can bind to a cellular Wnt nucleic acid sequence, e.g., mRNA, and inhibit expression of the protein, e.g., an antisense molecule or Wnt ribozyme; an antibody that specifically binds to Wnt protein, e.g., an antibody that disrupts Wnt's ability to bind to its natural cellular target, e.g., disrupts Wnt's ability to bind to Frizzled; an antibody that specifically binds to Frizzled, e.g., an antibody that disrupts Frizzled's ability to bind to Wnt; a mutated inactive Wnt protein or fragment which binds to Frizzled but does not activate the Wnt signaling pathway; an agent which decreases Wnt gene expression, e.g., a small molecule which binds the promoter of Wnt.

In another preferred embodiment, Wnt is inhibited by decreasing the level of expression of an endogenous Wnt gene, e.g., by decreasing transcription of the Wnt gene. In a preferred embodiment, transcription of the Wnt gene can be decreased by: altering the regulatory sequences of the endogenous Wnt gene, e.g., by the addition of a negative regulatory sequence (such as a DNA-binding site for a transcriptional repressor).

In a preferred embodiment, the agent which decreases the level of Wnt protein of inhibits an effect of Wnt promoted signal transduction is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the Wnt protein level or Wnt promoted signal transduction is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair growth is inhibited on: the subject's scalp; the subject's face, e.g., beard and/or mustache facial hair growth or eyebrow growth is inhibited; the subject's body hair growth is inhibited, e.g., hair growth is inhibited on the subject's back, legs, chest, armpits.

In another aspect, the invention features a method of promoting hair growth in a subject. The method includes activating or increasing activation of the Wnt-β-catenin signaling pathway.

In a preferred embodiment, activation of the Wnt-β-catenin pathway is increased by administering an agent which increases the level of Wnt protein production and/or which mimics an effect of Wnt promoted signal transduction, e.g., inhibition of β-catenin phosphorylation, e.g., by inhibition of GSK3β kinase, or accumulation of β-catenin. An agent which increases the level of Wnt protein and/or which mimics an effect of Wnt promoted signal transduction can be one or more of: a Wnt polypeptide or a functional fragment or analog thereof as described herein; a nucleotide sequence encoding a Wnt polypeptide or functional fragment or analog thereof as described herein; an agent which increases Wnt nucleic acid expression, e.g., a small molecule which binds to the promoter region of Wnt; an agent which mimics an effect of Wnt promoted signal transduction, e.g., inhibition of β-catenin phosphorylation, e.g., by inhibition of GSK3β kinase, or accumulation of β-catenin. Examples of agents which can mimic Wnt promoted signal transduction include inhibitors of GSK3β, e.g., lithium chloride or similar small ions, agents which bind Frizzled and mimic Wnt binding, e.g., anti-Frizzled antibodies, or other naturally or non-naturally occurring Frizzled binding ligands. In other embodiments, the level of Wnt protein can be increased by increasing the level of expression of an endogenous Wnt gene, e.g., by increasing transcription of the Wnt gene, as described herein. In another preferred embodiment, activation of the Wnt-β-catenin pathway is increased by administering: an agent which increases β-catenin protein production or activity, e.g., an agent which decreases phosphorylation of β-catenin and/or which increases β-catenin accumulation, e.g., a β-catenin polypeptide or a fragment or analog thereof, a nucleic acid sequence encoding a β-catenin polypeptide or fragments or analogs thereof; an agent which increases LEF-1 protein production and/or activity, e.g., an LEF-1 polypeptide or a fragment or analog thereof, a nucleic acid sequence encoding an LEF-1 polypeptide or fragments or analogs thereof.

In another preferred embodiment, the method can include introducing a cell, e.g., a cell which expresses and preferably secretes a protein involved in the activation of the Wnt-β-catenin signaling pathway, into a subject. In a preferred embodiment, the cell has been genetically modified to express: a Wnt protein, or a fragment or an analog thereof; a β-catenin protein, or fragment or analog thereof; an LEF-1 protein, or a fragment or analog thereof. In a preferred embodiment, the cell expresses a Wnt protein, e.g., a Wnt 3, Wnt 4, or Wnt 7, or a fragment or an analog thereof. In another preferred embodiment, the cell has been genetically modified to cause the expression of Wnt, e.g., the cell has been genetically modified to express a Wnt protein, or a fragment or an analog thereof, or the cell has been genetically modified to introduce a nucleic acid sequence, e.g., a regulatory sequence, e.g., a promoter or an enhancer, that causes or increases the expression of the endogenous Wnt. In a preferred embodiment, the promoter of the endogenous Wnt gene has been replaced by another promoter, e.g., by a promoter from another gene. The cell can be an autologous, allogeneic, or xenogeneic cell, but is preferably autologous. The autologous cell is preferably from a subject characterized with hair loss. The manipulated cell can be any cell type, e.g., a fibroblast, a keratinocyte, an epithelial cell. Preferably the cell is an epithelial cell, e.g., an epidermal cell, a hair follicle cell, a dermal papilla cell. The cell can be introduced into a subject to increase Wnt activity.

In a preferred embodiment, the level of Wnt, e.g., Wnt 3, Wnt 4, or Wnt 7, is increased over a sustained period of time, e.g., a period equal to or greater than 2, 10, 14, 30, 60, 90, or 180 days. E.g., a cell expressing a Wnt protein, fragment, or analog can be supplied, e.g., by any method described herein, whereby Wnt is released over a sustained period of time, e.g., a period equal to or greater than 2, 10, 14, 30, 60, 90, or 180 days. The cell can be introduced into a subject, e.g., to increase the level of the protein involved in activation of the Wnt-β-catenin signaling pathway.

In a preferred embodiment, the agent is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the Wnt-β-catenin signaling pathway is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair growth is promoted on: the subject's scalp; the subject's face, e.g., beard and/or mustache facial hair growth is promoted.

In a preferred embodiment, the subject has an insufficient amount of hair or an insufficient rate of hair growth. In a preferred embodiment, the subject suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

In another aspect, the invention features a method of inhibiting hair growth in a subject. The method includes inhibiting activation of the Wnt-β-catenin signaling pathway.

In a preferred embodiment, activation of the Wnt-β-catenin pathway is inhibited by administering an agent which decreases the level of Wnt protein production and/or decreases an effect of Wnt promoted signal transduction. An agent which inhibits the level of Wnt protein or is a Wnt antagonist can be one or more of: a Frizzled protein or binding portion thereof; a Wnt nucleic acid molecule which can bind to a cellular Wnt nucleic acid sequence, e.g., mRNA, and inhibit expression of the protein, e.g., an antisense molecule or Wnt ribozyme; an antibody that specifically binds to Wnt protein, e.g., an antibody that disrupts Wnt's ability to bind to its natural cellular target, e.g., disrupts Wnt's ability to bind to a Frizzled receptor protein; an antibody that specifically binds to Frizzled, e.g., an antibody that disrupts a Frizzled's ability to bind to Wnt; a mutated inactive Wnt protein or fragment which binds to Frizzled but does not activate the Wnt signaling pathway; an agent which decreases Wnt gene expression, e.g., a small molecule which binds the promoter of Wnt; an agent which decreases an activity of Wnt, e.g., an agent which increases phosphorylation of β-catenin. In other embodiments, the level of Wnt protein can be inhibited by decreasing the level of expression of an endogenous Wnt gene, e.g., by decreasing transcription of the Wnt gene, as described herein. In another preferred embodiment, activation of the Wnt-β-catenin pathway is inhibited by administering: an agent which inhibits β-catenin protein production or inhibits an effect of Wnt promoted signal transduction, e.g., an agent which increases phosphorylation of β-catenin and/or which decreases β-catenin accumulation; an agent which inhibits LEF-1 protein production and/or activity.

In a preferred embodiment, the agent is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the effect on the Wnt-β-catenin signaling pathway is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair growth is inhibited on: the subject's scalp; the subject's face, e.g., beard and/or mustache facial hair growth or eyebrow growth is inhibited; the subject's body hair growth is inhibited, e.g., hair growth is inhibited on the subject's back, legs, chest, armpits.

In another aspect, the invention features a method of evaluating the status of hair growth/hair loss in a subject. The method includes evaluating, e.g., detecting, the presence or absence of a genetic lesion in a Wnt gene, or evaluating, e.g., detecting, misexpression of the Wnt gene.

In one embodiment, the method includes evaluating whether a subject is at risk for hair loss. The method includes evaluating, e.g., detecting, a genetic lesion in a Wnt gene, or evaluating, e.g., detecting, underexpression of the Wnt gene, to thereby determine if a subject is at risk for hair loss.

In a preferred embodiment, the Wnt gene or protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In preferred embodiment, the method includes evaluating in a sample of cells from the subject for the presence or absence of a genetic lesion, e.g., a mutation in the gene encoding a Wnt protein. The presence of a genetic lesion is indicative of a risk of hair loss in a subject. The cell sample can be of any cell type, e.g., a fibroblast, a keratinocyte, an epithelial cell, an endothelial cell, a glial cell, a neural cell, a lymphocyte, a bone marrow cell, and a muscle cell.

In another preferred embodiment, the method includes evaluating in a sample of cells, e.g., a sample of epidermal cells from the hair follicle of a subject, for the expression levels of the Wnt to determine underexpression. Underexpression of Wnt is indicative of a risk of hair loss.

In a preferred embodiment, the genetic lesions is evaluated by contacting the sample with a nucleic acid probe capable of hybridizing to Wnt mRNA, e.g., a labeled probe. In another preferred embodiment, expression of Wnt is evaluated with an antibody capable of binding to Wnt protein, e.g., a labeled antibody.

In another embodiment, the method includes evaluating hair growth in a subject. The method includes evaluating, e.g., detecting, absence or presence of a genetic lesion in a Wnt gene, or evaluating, e.g., detecting, overexpression of the Wnt gene, to thereby evaluate whether hair growth is likely in a subject.

In a preferred embodiment, the Wnt gene or protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, the method includes evaluating in a sample of cells from the subject for the presence or absence of a genetic lesion, e.g., a mutation in the gene encoding a Wnt protein. The absence of a genetic lesion is indicative of a potential for hair growth. The cell sample can be of any cell type, e.g., a fibroblast, a keratinocyte, an epithelial cell, an endothelial cell, a glial cell, a neural cell, a lymphocyte, a bone marrow cell, and a muscle cell.

In another preferred embodiment, the method includes evaluating in a sample of cells, e.g., a sample of epidermal cells from the hair follicle of a subject, for the expression levels of Wnt to determine overexpression. Overexpression of Wnt is indicative of a potential for hair growth.

In a preferred embodiment, the genetic lesions is evaluated by contacting the sample with a nucleic acid probe capable of hybridizing to Wnt mRNA, e.g., a labeled probe. In another preferred embodiment, expression of Wnt is evaluated with an antibody capable of binding to Wnt protein, e.g., a labeled antibody.

In another aspect, the invention features a method of evaluating the ability of an epidermal cell to promote hair growth or hair loss in a subject. The method includes evaluating, e.g., detecting, the presence or absence of a genetic lesion in a Wnt gene, or evaluating, e.g., detecting, misexpression of the Wnt gene.

In a preferred embodiment, the ability of an epidermal cell to promote hair growth or hair loss is evaluated in vitro.

In one embodiment, the method includes evaluating the ability of an epidermal cell to promote hair loss. The method includes evaluating, e.g., detecting, a genetic lesion in a Wnt gene, or evaluating, e.g., detecting, underexpression of the Wnt gene.

In a preferred embodiment, the Wnt gene or protein is: Wnt3, e.g., Wnt3a or Wnt 3b; Wnt 4; Wnt 7, e.g., Wnt 7a or 7b. In a particularly preferred embodiment, the Wnt protein is Wnt 3, most preferably, Wnt3a.

In preferred embodiment, the method includes evaluating in a sample of epidermal cells from the subject for the presence or absence of a genetic lesion, e.g., a mutation in the gene encoding a Wnt protein. The presence of a genetic lesion is indicative of a risk of hair loss in a subject.

In another preferred embodiment, the method includes evaluating in a sample of epidermal cells, for the expression levels of the Wnt to determine underexpression. Underexpression of Wnt is indicative of a risk of hair loss.

In a preferred embodiment, the genetic lesions is evaluated by contacting the sample with a nucleic acid probe capable of hybridizing to Wnt mRNA, e.g., a labeled probe. In another preferred embodiment, expression of Wnt is evaluated with an antibody capable of binding to Wnt protein, e.g., a labeled antibody.

In another embodiment, the method includes evaluating the ability of an epidermal cell to promote hair growth. The method includes evaluating, e.g., detecting, absence or presence of a genetic lesion in a Wnt gene, or evaluating, e.g., detecting, overexpression of the Wnt gene.

In a preferred embodiment, the Wnt gene or protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably, Wnt3a.

In a preferred embodiment, the method includes evaluating in a sample of epidermal cells from the subject for the presence or absence of a genetic lesion, e.g., a mutation in the gene encoding a Wnt protein. The absence of a genetic lesion is indicative of a potential for hair growth.

In another preferred embodiment, the method includes evaluating in a sample of epidermal cells for the expression levels of Wnt to determine overexpression. Overexpression of Wnt is indicative of a potential for hair growth.

In a preferred embodiment, the genetic lesions is evaluated by contacting the sample with a nucleic acid probe capable of hybridizing to Wnt mRNA, e.g., a labeled probe. In another preferred embodiment, expression of Wnt is evaluated with an antibody capable of binding to Wnt protein, e.g., a labeled antibody.

In another aspect, the invention features a method for identifying a compound capable of promoting hair growth. The method includes: contacting a cell capable of expressing a Wnt polypeptide with a test compound; and determining the level of Wnt polypeptide or nucleic acid expression, wherein a compound capable of increasing Wnt polypeptide or nucleic acid expression is indicative of a compound capable of promoting hair growth.

In a preferred embodiment, the Wnt protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, the compound is a Wnt fragment or analog.

In a preferred embodiment, the method further includes evaluating a control cell, e.g., an identical cell which is not treated with the compound.

In a preferred embodiment, the cell is: an epidermal cell, e.g., an epidermal cell from a hair follicle; a DP cell.

In a preferred embodiment, Wnt nucleic acid expression is evaluated using a nucleic acid probe, e.g., a labeled probe, capable of hybridizing to a Wnt nucleic acid molecule, e.g., Wnt mRNA. In a preferred embodiment, Wnt nucleic acid expression, e.g., DNA expression, is evaluated by contacting a compound with a Wnt nucleic acid molecule, e.g., a regulatory sequence of a Wnt nucleic acid molecule, and evaluating Wnt transcription, in vitro or in vivo, e.g., Wnt transcription is evaluated by determining a cell activity, e.g., using a marker gene, e.g., a lacZ gene or green fluorescence protein (GFP) gene, fused to the regulatory sequence of Wnt and following production of the marker.

In a preferred embodiment, Wnt polypeptide expression is evaluated using an anti-Wnt antibody, e.g., a labeled anti-Wnt antibody.

In another aspect, the invention features a method for identifying a compound capable of inhibiting hair growth. The method includes: contacting a cell capable of expressing a Wnt polypeptide with a test compound; and determining the level of Wnt polypeptide or nucleic acid expression in the presence and absence of the compound, wherein a compound capable of decreasing Wnt polypeptide or nucleic acid expression is indicative of a compound capable of inhibiting hair growth.

In a preferred embodiment, the Wnt polypeptide is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, Wnt nucleic acid expression is evaluated using a nucleic acid probe, e.g., a labeled probe, capable of hybridizing to a Wnt nucleic acid molecule, e.g., Wnt mRNA. In preferred embodiment, Wnt nucleic acid expression, e.g., DNA expression, is evaluated by contacting a compound with a Wnt nucleic acid molecule, e.g., a regulatory sequence of a Wnt nucleic acid molecule, and evaluating Wnt transcription, in vitro or in vivo, Wnt transcription is evaluated by determining a cell activity, e.g., using a marker gene, e.g., a lacZ gene or a GFP gene, fused to the regulatory sequence of Wnt and following production of the marker.

In a preferred embodiment, Wnt polypeptide expression is evaluated using an anti-Wnt antibody, e.g., a labeled anti-Wnt antibody.

In another aspect, the invention features a method of culturing a DP cell. For example, a human or non-human, e.g., rodent, e.g., rat or mouse, DP cell. The method includes culturing the DP cell in the presence of an increased level of Wnt, another protein involved in activating the Wnt-β-catenin signaling pathway, e.g., β-catenin and/or LEF-1, and/or an agent which mimics an effect of Wnt promoted signal transduction, e.g., inhibition of β-catenin phosphorylation, e.g., by inhibition of GSK3β kinase, or accumulation of β-catenin.

In a preferred embodiment, the level of Wnt is increased over DP cells in the absence of Wnt.

In a preferred embodiment, the Wnt protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, the DP cell is propagated in vitro. In a preferred embodiment, the DP cell is cultured to increase the number of DP cells.

In a preferred embodiment, a Wnt polypeptide or a functional fragment or analog thereof is added to the culture. In another preferred embodiment, an agent which mimics an effect of Wnt promoted signal transduction, e.g., inhibition of β-catenin phosphorylation, e.g., by inhibition of GSK3β kinase, or accumulation of β-catenin, is added to the culture. Examples of agents which can mimic an effect of Wnt promoted signal transduction include inhibitors of GSK3β kinase such as lithium chloride or similar small ions.

In another preferred embodiment, the DP cell is cultured in the presence of a cell which expresses a Wnt polypeptide or a functional fragment or analog thereof.

In a preferred embodiment, the DP cell is obtained from a subject, cultured with an increased level of Wnt, or an agent which mimics an effect of Wnt promoted signal transduction, e.g., inhibition of β-catenin phosphorylation, e.g., by inhibition of GSK3β kinase, or accumulation of β-catenin, and then returned to the same or a different subject.

In a preferred embodiment, the DP cell is maintained in culture and then the cultured DP cells are returned to the same or a different subject to increase the amount of hair growth in the individual.

In another preferred embodiment, the invention features a method of providing and maintaining a dermal papilla cell graft, e.g., a DP graft for hair transplantation procedures. The method includes culturing a DP cell or DP cells in the presence of Wnt or a fragment or analog thereof, another protein involved in activating the Wnt-β-catenin signaling pathway (e.g., β-catenin and/or LEF-1) or a fragment or analog thereof, and/or an agent which mimics an effect of Wnt promoted signal transduction, e.g., inhibition of β-catenin phosphorylation, e.g., by inhibition of GSK3β kinase, or accumulation of β-catenin.

In a preferred embodiment, the DP cell is propagated in vitro. In a preferred embodiment, the DP cell is propagated in vitro to increase the number of DP cells.

In a preferred embodiment, a Wnt polypeptide or a functional fragment or analog thereof is added to the culture. In another preferred embodiment, an agent which mimics an effect of Wnt promoted signal transduction, e.g., inhibition of β-catenin phosphorylation, e.g., by inhibition of GSK3β kinase, or accumulation of β-catenin, is added to the culture. Examples of agents which mimic an effect of Wnt promoted signal transduction include inhibitors of GSK3β kinase such as lithium chloride or similar small ions.

In another preferred embodiment, the DP cell is cultured in the presence of a cell which expresses a Wnt polypeptide or a functional fragment or analog thereof.

In a preferred embodiment, the DP cell is obtained from a subject, cultured with an increased level of Wnt, or an agent which mimics an effect of Wnt promoted signal transduction, e.g., inhibition of β-catenin phosphorylation, e.g., by inhibition of GSK3β kinase, or accumulation of β-catenin, and then returned to the same or a different subject.

In another aspect, the invention features a media for culturing DP cells which includes a Wnt polypeptide or a functional fragment or analog thereof, or an agent which mimics an effect of Wnt promoted signal transduction, e.g., inhibition of β-catenin phosphorylation, e.g., by inhibition of GSK3β kinase, or accumulation of β-catenin. Examples of agents which mimic an effect of Wnt promoted signal transduction include inhibitors of GSK3β kinase such as lithium chloride or similar small ions.

In another aspect, the invention features a method of promoting or maintaining anagen phase gene expression of DP cells. The method includes increasing the level of Wnt protein or mimicking an effect of Wnt promoted signal transduction, e.g., inhibition of β-catenin phosphorylation, e.g., by inhibition of GSK3β kinase, or accumulation of β-catenin, to thereby promote or maintain anagen phase gene expression in the DP cells. In another preferred embodiment, the method includes increasing activation of the Wnt-β-catenin signaling pathway, to thereby promote or maintain anagen phase gene expression in DP cells.

In a preferred embodiment, the Wnt protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, Wnt level is increased or an effect of Wnt promoted signal transduction is mimicked by administering an agent which increases the level of Wnt protein production and/or which mimics an effect of Wnt promoted signal transduction, e.g., inhibition of β-catenin phosphorylation, e.g., by inhibition of GSK3β kinase, or accumulation of β-catenin. An agent which increases the level of Wnt protein and/or mimics an effect of Wnt promoted signal transduction can be one or more of: a Wnt polypeptide or a functional fragment or analog thereof, as described herein; a nucleotide sequence encoding a Wnt polypeptide or functional fragment or analog thereof, as described herein; an agent which increases Wnt nucleic acid expression, e.g., a small molecule which binds to the promoter region of Wnt; an agent which mimics an effect of Wnt promoted signal transduction, e.g., inhibition of β-catenin phosphorylation, e.g., by inhibition of GSK3β kinase, or accumulation of β-catenin.

Examples of agents which can mimic Wnt promoted signal transduction include inhibitors of GSK3β, e.g., lithium chloride or similar small ions, agents which bind Frizzled and mimic Wnt binding, e.g., anti-Frizzled antibodies, or other naturally or non-naturally occurring Frizzled binding ligands.

In a preferred embodiment, the method can be performed in vitro or in vivo. For example, the DP cells can be maintained in anagen phase in culture, and then administered to a subject, e.g., to increase hair growth. Such methods can include maintaining DP cells in culture in the presence of Wnt or an agent which mimics an effect of Wnt promoted signal transduction, e.g., inhibition of β-catenin phosphorylation, e.g., by inhibition of GSK3β kinase, or accumulation of β-catenin. In one embodiment, Wnt and/or an agent which mimics an effect of Wnt promoted signal transduction, e.g., an inhibitor of GSK3β kinase, e.g., lithium chloride or similar small ions, can be added to the culture. In another embodiment, the DP cell can be co-cultured with a cell which expresses Wnt, e.g., a cell which naturally expressed Wnt or has been genetically engineered to express Wnt. DP cells maintained in anagen phase can then be used, e.g., in DP graft procedures. The DP cells can be obtained from the subject who will be receiving the DP graft (i.e., autologous cells), or can be obtained from a different subject (e.g., allogeneic or xenogeneic cells).

In a preferred embodiment, Wnt is increased by administering, e.g., introducing, a nucleotide sequence encoding a Wnt polypeptide or functional fragment or analog thereof, into a particular cell, e.g., an epidermal cell or a DP cell, and/or into a subject. The nucleotide sequence can be a genomic sequence or a cDNA sequence. The nucleotide sequence can include: a Wnt coding region; a promoter sequence, e.g., a promoter sequence from a Wnt gene or from another gene; an enhancer sequence, e.g., 5' untranslated region (UTR), e.g., a 5' UTR from a Wnt gene or from another gene, a 3' UTR, e.g., a 3' UTR from a Wnt gene or from another gene; a polyadenylation site; an insulator sequence.

In another preferred embodiment, the level of Wnt protein is increased by increasing the level of expression of an endogenous Wnt gene, e.g., by increasing transcription of the Wnt gene. In a preferred embodiment, transcription of the Wnt gene is increased by: altering the regulatory sequences of the endogenous Wnt gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Wnt gene to be transcribed more efficiently.

In another preferred embodiment, the method can include introducing a cell, e.g., a cell which expresses and preferably secretes a Wnt protein, into a subject. In a preferred embodiment, the cell has been genetically modified to express a Wnt protein, or a fragment or an analog thereof. The cell can be an autologous, allogeneic, or xenogeneic cell, but is preferably autologous. The cell can be any cell type, e.g., a fibroblast, a keratinocyte, an epithelial cell, an endothelial cell. Preferably the cell is an epithelial cell, e.g., an epidermal cell or a DP cell. The cell can be introduced into a subject to increase the level of Wnt protein.

In a preferred embodiment, the agent which increases the level of Wnt protein and/or mimics an effect of Wnt promoted signal transduction is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the Wnt protein level is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, anagen phase gene expression is promoted or maintained in: the subject's scalp; the subject's face, e.g., upper lip and/or chin.

In another aspect, the invention features a method of promoting or maintaining hair inductive activity. The method includes increasing the level of Wnt protein and/or mimicking an effect of Wnt promoted signal transduction, e.g., inhibition of β-catenin phosphorylation, e.g., by inhibition of GSK3β kinase, or accumulation of β-catenin, to thereby promote or maintain hair inductive activity.

In a preferred embodiment, the Wnt protein is: Wnt3, e.g., Wnt3a or Wnt 3b; Wnt 4; Wnt 7, e.g., Wnt 7a or 7b. In a particularly preferred embodiment, the Wnt protein is Wnt3, most preferably Wnt3a.

In a preferred embodiment, Wnt is increased by administering an agent which increases the level of Wnt protein production and/or activity. An agent which increases the level of Wnt protein can be one or more of: a Wnt polypeptide or a functional fragment or analog thereof; a nucleotide sequence encoding a Wnt polypeptide or functional fragment or analog thereof; an agent which increases Wnt nucleic acid expression, e.g., a small molecule which binds to the promoter region of Wnt; an agent which mimics an effect of Wnt promoted signal transduction, e.g., inhibition of β-catenin phosphorylation, e.g., by inhibition of GSK3β kinase, or accumulation of β-catenin. Examples of agents which mimic an effect of Wnt promoted signal transduction include inhibitors of GSK3β kinase such as lithium chloride or similar small ions In a preferred embodiment, Wnt is increased by administering, e.g., introducing, a nucleotide sequence encoding a Wnt polypeptide or functional fragment or analog thereof, into a particular cell, e.g., an epidermal cell or a DP cell, in the subject. The nucleotide sequence can be a genomic sequence or a cDNA sequence. The nucleotide sequence can include: a Wnt coding region; a promoter sequence, e.g., a promoter sequence from a Wnt gene or from another gene; an enhancer sequence, e.g., 5' untranslated region (UTR), e.g., a 5' UTR from a Wnt gene or from another gene, a 3' UTR, e.g., a 3' UTR from a Wnt gene or from another gene; a polyadenylation site; an insulator sequence.

In another preferred embodiment, the level of Wnt protein is increased by increasing the level of expression of an endogenous Wnt gene, e.g., by increasing transcription of the Wnt gene. In a preferred embodiment, transcription of the Wnt gene is increased by: altering the regulatory sequences of the endogenous Wnt gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Wnt gene to be transcribed more efficiently.

In another preferred embodiment, the method can include introducing a cell, e.g., a cell which expresses and preferably secretes a Wnt protein, into a subject. In a preferred embodiment, the cell has been genetically modified to express a Wnt protein, or a fragment or an analog thereof. The cell can be an autologous, allogeneic, or xenogeneic cell, but is preferably autologous. The cell can be any cell type, e.g., a fibroblast, a keratinocyte, an epithelial cell, an endothelial cell. Preferably the cell is an epithelial cell, e.g., an epidermal cell or a DP cell. The cell can be introduced into a subject to increase the level of Wnt protein and/or to mimic an effect of Wnt promoted signal transduction.

In a preferred embodiment, the agent which increases the level of Wnt protein and/or mimics Wnt promoted signal transduction is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the Wnt protein level and/or the Wnt signaling pathway is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair inductive activity is promoted or maintained on: the subject's scalp; the subject's face, e.g., upperlip and/or chin.

A "treatment", as used herein, includes any therapeutic treatment, e.g., the administration of a therapeutic agent or substance, e.g., a drug.

The term "increasing hair growth" as used herein refers to increasing the number or density or distribution of follicles or hair shafts or otherwise increasing the growth of hair.

As used herein, the term "subject" refers an animal, e.g., a mammal, e.g., a human. The mammal can be a human or non-human mammal, e.g., a swine, a bird, a cat, a dog, a monkey, a goat, or a rodent, e.g., a rat or a mouse. The animal can be a transgenic animal, e.g., a transgenic rodent, e.g., a transgenic rat or mouse.

"Regulatory sequence" refers to any or all of the DNA sequences that controls gene expression. An example of a regulatory sequence includes: a promoter, a positive regulatory element (such as an enhancer or a DNA-binding site for a transcriptional activator); a negative regulatory element (such as a DNA-binding site for a transcriptional repressor) and an insulator.

"Heterologous" refers to DNA or tissue which is derived from a different species.

"Heterologous regulatory sequence" refers to a sequence which is not the normal regulatory sequence of that gene The terms "peptides", "proteins", and "polypeptides" are used interchangeably herein.

The term "small molecule", as used herein, includes peptides, peptidomimetics, or non-peptidic compounds, such as organic molecules, having a molecular weight less than 2,000, preferably less than 1,000.

The term "effects of Wnt-promoted signal transduction" refers to one or more of the biochemical effects (e.g., modulation of e.g., protein binding interactions, phosphorylation or transcription) in a cell, e.g., a DP cell, initiated by Wnt signaling, e.g., by Wnt binding to Frizzled. Effects of Wnt promoted signal transduction can include Wnt binding to Frizzled; inhibition of GSK3β mediated phosphorylation; inhibition of phosphorylation-dependent degradation of β-catenin; accumulation of β-catenin protein in the cytoplasm; stabilization of cellular β-catenin; β-catenin accumulation in the cytoplasm; β-catenin binding to Lef1; translocation of the β-catenin-Lef1 complex to the nucleus; and stimulation of transcription from associated genes. Components of Wnt-promoted signal transduction can include Frizzled protein, e.g., Frizzled-7 (frz-7), disheveled proteins, e.g., disheveled-2 (dsh-2), GSK3, beta catenin, Lef1, and Lef/TFC. Other effects and components of the Wnt signaling pathway are described in Arias et al. (1999) *Curr. Opin. Genet. & Dev.* 9:447-454, which is incorporated herein by reference.

Other features and advantages of the invention will be apparent from the following detailed description, and from the claims.

DETAILED DESCRIPTION OF THE INVENTION

The present invention is based, in part, on the discovery that Wnt proteins expressed in the follicular epithelium maintain anagen phase gene expression in dermal papilla cells and that hair inductive activity is also maintained by Wnt signaling.

Both formation of the hair follicle during embryonic development and the cyclical growth, quiescence and regeneration of the hair shaft during the hair cycle are dependent on reciprocal signaling between the epidermal and dermal components of the follicle.

In the Wnt signaling pathway, Wnt, which is a soluble molecule, binds Frizzled (Frz), a cell surface receptor, found on various types of cells. In the presence of disshelved, binding of Wnt to Frz results in the inhibition of GSK3β mediated phosphorylation and subsequent phosphorylation-dependent degradation of β-catenin. Thus, Wnt binding stabilizes cellular β-catenin. In the presence of Wnt binding, β-catenin accumulates in the cytoplasm and binds to Lef1. The β-catenin-Lef1 complex then translocates to the nucleus, where it mediates transcriptional activation.

Production of a Transgenic Mouse Expressing Green Fluorescent Protein in DP Cells A transgenic mouse line that specifically expresses green fluorescent protein (GFP) in DP cells during the anagen (growth) phase of the hair cycle was used to purify GFP expressing DP cells and study the signals required to maintain GFP expression. The transgenic mouse line was generated as described in Kishimoto et al. (1999) *Proc. Natl. Acad. Sci USA* 96:7336-7341. It was found that isolated transgenic anagen hair follicles show GFP fluorescence in the DP. The versican-GFP transgene is active during anagen but is shut off during catagen and telogen of hair growth. Therefore, transgene expression was correlated with the presumed profile of inductive activity in the DP.

RT-PCR Analysis

Total RNA was isolated and RT PCR performed as described in Kishimoto et al. (1999) *Proc. Natl Acad. Sci. USA* 96:7336-7341, using an annealing temperature of 58° C. The primers employed are listed below. With the exception of Wnts 4, 5 and 7, the primers were designed to distinguish between mouse and chicken orthologues and the lack of cross reaction to chick sequences was confirmed on cDNA from feeder cells alone.

```
Wnt3:
G CGC CCT GGC TCA CTA C                    (SEQ ID NO: 1)
and

ATG CTG CTG CTG CTG GCC                    (SEQ ID NO: 2)
                                           for 30 cycles Wnt4:
TGA TCC AGA GGC AGG TGC AG                 (SEQ ID NO: 3)
and CTT CTC CAG TTC TCC ACT GC                 (SEQ ID NO: 4)
                                           for 36 cycles Wnt5a:
CTG TTG AC TGC ACC AGC TT                  (SEQ ID NO: 5)
and TCA AGG AAT GCC AGT ACC AGT ACC AG         (SEQ ID NO: 6)
                                           for 30 cycles Frizzled-7:
CTG CTA GAG GAC CGT GCC                    (SEQ ID NO: 7)
and AGG TGC GTT CCC AGT GCT                    (SEQ ID NO: 8)
                                           for 36 cycles Disheveled-2:
CAT CCT TCA GCA GTG TCA                    (SEQ ID NO: 9)
and CGT CAT TGT CAT TCA GAG                    (SEQ ID NO: 10)
                                           for 36 cycles GSK-3β:
CAG GGC ACC AGA GTT GAT                    (SEQ ID NO: 11)
and GCA GAA GCG GCG TTA TTG                    (SEQ ID NO: 12)
                                           for 30 cycles β-catenin:
CCA CCA GCT AGG CGC ACT                    (SEQ ID NO: 13)
and GGG CTC AGA GGG TCC GAG                    (SEQ ID NO: 14)
                                           for 30 cycles LEF-1:
ACT GTC AGG CGA CAC TTC C                  (SEQ ID NO: 15)
and TGC ACG TTG GGA AGG AGC                    (SEQ ID NO: 16)
                                           for 36 cycles Shh:                                       for 30 cycles
                                           (SEQ ID NO: 17 &
                                           18)

Patched-1:
AGC TCA ACA GTA ACA CCC                    (SEQ ID NO: 20)
and

TGT TCT CCT CCA GCA TGA                    (SEQ ID NO: 21)
                                           for 36 cycles Gli-1:
TTG GGG ATG CTG GAT GGG                    (SEQ ID NO: 22)
and CGG TCA CTG GCA TTG CTA                    (SEQ ID NO: 23)
                                           for 36 cycles β-actin:
5'-CCA CAC CCG CCA CCA GTT C-3'            (SEQ ID NO: 24)
and 5'-GAGGAAGAGGATGCGGCA-3'                   (SEQ ID NO: 25)
                                           for 26 cycles

GFP:
5'-TGCAGTGCTTCAGCCGCTAC-3'                 (SEQ ID NO: 26)
AND

5'-CTCGTTGGGGTCTTTGCTCA-3'                 (SEQ ID NO: 27)
                                           for 26 cycles.
```

Cell Culture

Fresh mouse pelage DP cells were obtained from versican GFP transgenic newborn skin by high-speed cell sorting (Mo-FLO) as described previously in Kishimoto et al., supra. Chick embryo fibroblasts (CEFs) were infected with RCASBP(A) retroviral vectors encoding chick Shh, as described in Riddle et al. (1993) *Cell* 75:1401-1416, Wnt3a, as described in Kengaku et al. (1998) *Science* 280:1274-1277, Wnt4, Wnt5a (Noramly and Morgan, in prep), or Wnt7a, as described in Riddle et al. (1995) *Cell* 83:631-640, or vector alone as described, as described in Morgan et al. in *Methods in Cell Biology* (ed. Bonner-Fraser) pp. 185-218 (Academic Press, San Diego, 1996). GFP positive mouse DP cells were added onto 30-50% confluent feeder cells to achieve a ratio of 1:3 (mouse:chick). For the flow cytometric analysis, cells were co-cultured in 24 well dishes for 48-96 hrs. For the grafting experiment co-cultured cells were passaged 2-3 times in 10 cm dishes to generate the $2\times10^6$ cells required for each graft.

Flow Cytometry

Cells were trypsinized and resuspended in 0.5 ml PBS with 1% BSA. Flow cytometric analysis was performed by FACScan (Becton Dickinson). DP cells were labeled with mouse MHC class II monoclonal antibody and incubated with secondary IgG conjugated to PE. The PE negative avian cells fell below the lower gate in FIG. 3 and were excluded from the analysis of GFP expression.

Reconstitution Assay

The reconstitution assay was performed as described in Kishimoto et al., supra. Primary keratinocytes were prepared from 2 newborn pups per graft and combined with $2\times10^6$ DP cells in the graft chamber. Hair growth was monitored two weeks after grafting and weekly thereafter.

Production of Cell Culture of GFP Expressing DP Cells

Anagen dermal papilla cells from the skin of the transgenic mouse described above were purified to homogeneity using a fluorescence activated cell sorter and were shown to retain hair inductive activity in a skin reconstitution assay. However, using flow cytometric analysis of GFP expression in DP cells immediately after isolation and after 90 hours in culture, it was found that the inductive activity and GFP expression of the DP cells were rapidly lost in culture. This suggests that a factor normally supplied by epidermal cells was required to maintain DP cells in the anagen state.

Analysis of the Role of Shh in Anagen Phase

One candidate for the signal supplied by the epidermal cells was Shh, which is expressed in the epidermal component of the hair follicle and is required for the maturation of the dermal papilla during embryonic development. See, e.g., St. Jacques (1998) *Curr. Biol.* 8:1058-1068. During the hair cycle, exogenous Shh can accelerate the transition from telogen to anagen. Sato et al. (1999) *J. Clin. Invest.* 104:855-864. Expression of Shh, patched-1 (ptc-1), Gli-1 and the control of β-actin genes was analyzed in DP cells immediately after isolation and after three passages in culture. In skin from newborn transgenic mice undergoing active hair growth, Shh mRNA was detected in the GFP negative population of sorted cells, which includes follicular epidermis, and was absent from the dermal papilla cells. Ptc-1 and Gli-1 are expressed in isolated DP but transcription levels decreased upon passage in culture. Transcriptional feedback in the Shh signal transduction cascade results in increased accumulation of mRNA encoding two of its components, patched (ptc) and Gli-1, in response to Shh signaling. This induction serves as an indication of response to the Shh signal. Goodrich et al. (1996) *Genes Dev.* 10:301-312; Marigo et al. (1996) *Development* 122:1225-1233. Message from both genes was readily detected in freshly sorted DP cells, but the abundance of both messages decreases to undetectable levels when isolated DP cells were cultured in the absence of follicular epithelium. Thus, Shh signaling from follicular epithelium to the dermal papilla occurs in the hair follicle and could cause DP activation in anagen. Therefore, it was evaluated whether Shh signaling was sufficient to rescue either GFP gene expression or hair inductive activity in DP cells maintained in culture. Freshly isolated DP cells were co-cultured with CEFs expressing Shh or infected with a control vector. The use of heterospecific feeder cells allowed analyzation of gene expression in the DP cells by PCR with species-specific primers and confirms that the DP cells received the Shh signal as demonstrated by induction and maintenance of both ptc-1 and Gli-1, while expression of both genes is decreased in DP cells co-cultured with control feeders. β-actin sequences were used to normalize input cDNA and murine specific primers were employed to discriminate between gene expression in the DP and feeder cell populations. However, as demonstrated by flow cytometric analysis of DP cells co-cultures with feeder layers producing Wnt3 or Shh or infected with control vectors, GFP expression declined at identical rates in Shh treated and control populations. In addition, the ratio of GFP positive and GFP negative cells was confirmed for each treatment. To confirm the correlation between GFP expression and maintenance of the anagen state, these cells were mixed with keratinocytes and grafted in bubble chambers on the backs of nude mouse hosts. In this assay, the hairless skin which forms in the absence of active DP cells was observed whether or not the DP cells had been cultured in the presence of Shh. Both grafts of control or Shh treated DP cells showed only occasional hairs three weeks after grafting to the nude mouse model. See Table 1.

As in vivo experiments have suggested that Shh stimulates the transition from telogen to anagen, it was also assessed whether Shh signaling was sufficient to activate isolated DP cells which had been maintained in culture until they were formally analogous to telogen DP cells in that both GFP expression and hair inductive activity were lost. Again, no change in either property was observed. Thus, although Shh may initiate anagen in vivo, it is likely that it acts on the DP in part indirectly, possibly by induction of a secondary signal in the epidermis.

Analysis of the Role of Wnt in Anagen Phase

A search of the sequence in the versican enhancer used to drive GFP expression in the DP revealed a Lef/TCF binding motif and suggested that a Wnt might serve as the signal from the epidermis which activates the DP cells. This binding site appears to be required for GFP expression because no GFP expression was observed in ten independent transgenic lines when this region was deleted from the expression construct. However, deletions from elsewhere in the construct had no effect on GFP expression in transgenic mice. The Lef/TCF family of DNA binding proteins mediates the transcriptional effects of Wnt signaling through the β-catenin pathway. Arias et al. (1999) *Curr. Opin. Genet. & Dev.* 9:447-454. Wnts are secreted glycoproteins which bind to Frizzled. In a process dependent on disheveled proteins, Frizzled receptor engagement inhibits phosphorylation of β catenin by a complex including GSK3. This results in accumulation of β-catenin protein in the cytoplasm and translocation to the nucleus where it can bind Lef/TCF and stimulate transcription from associated genes. In freshly isolated DP cells, Frizzled-7 (frz-7), disheveled-2 (dsh-2), GSK3, β catenin, Lef1 and the GFP transgene are all expressed. Thus, the components of this signal transduction cascade were expressed in freshly isolated DP cells. After three passages, expression of frz-7, dsv-2 and Lef1 are reduced. Furthermore, Wnt3a is expressed in the follicular matrix cells and Wnt3a, 5a and 7a transcripts were detected in the GFP negative population from dissociated skin which includes the follicular epithelia from anagen hair follicles. Thus, all of these Wnts are candidates to mediate signaling to the dermal papilla.

Feeder cells expressing Wnts 3a, 4, 5a or 7a were used to test the effects of Wnt signaling on freshly isolated DP cells. Co-culture with Wnts3a or 7a resulted in maintenance of GFP fluorescence in the majority of the DP cells as demonstrated by FACS analysis. RT PCR confirmed that this reflects increased levels of GFP RNA rather than stabilization of the encoded protein. In particular, GFP RNA levels are maintained by exposure to Wnt3a but not Shh or control feeder layers. Wnt 4 expressing cells also showed some maintenance of GFP expression but were less potent than either Wnt3a or 7a, while Wnt5a had no effect on DP GFP expression. As suggested by GFP expression, the hair inductive activity of DP cells was also maintained in culture by Wnt signaling. When the murine DP cells were resorted, combined with keratinocytes and used to reconstitute skin on a nude mouse host, Wnt3a or 7a treated cells showed a dramatic increase in hair growth compared to cells co-cultured with control feeders or Shh expression cells. The control and Shh treated DP cell grafts only showed an occasional hair three weeks after grafting, whereas DP cells exposed to Wnt3a formed a dense patch of hair in the graft. See Table 1.

While Wnt3a is sufficient to maintain DP cells in the anagen state, it cannot reactivate GFP expression or hair inductive activity in cells which have lost these properties in culture (data not shown). Analysis of transcripts encoding components of the Wnt signal transduction cascade reveals that Lef-1, disheveled-2 and Frizzled-7 are all down-regulated after maintenance in culture in the absence of Wnts and this could explain the failure of exogenous Wnt to reactivate GFP expression in these cells. Maintenance of expression of proteins required for Wnt signal transduction by other factors expressed locally in the epidermis could contribute to the coordination of morphogenesis in the follicle. The findings reported here suggest the possibility that a single Wnt expressed in the epidermis could coordinate development in both the dermis and epidermis.

The results demonstrate that Wnt3a, and possibly other Wnts, expressed in the anagen hair follicle can act as inductive signals to maintain the dermal papilla in an anagen state. The results also suggest that Shh signaling is not sufficient to initiate or maintain the anagen state of DP cells, and may therefore act at least in part indirectly to promote the transition to anagen in vivo. Finally these results extend the correlation between GFP expression in these transgenic DP cells and their ability to induce hair growth and thus suggest further use of this approach to dissect signaling between epithelia and mesenchyme to coordinate morphogenesis.

Wnt Polypeptides and Nucleic Acid Sequences Encoding Wnt

Wnt polypeptides can be obtained in several ways including isolation of Wnt or expression of a sequence encoding Wnt by genetic engineering methods. The nucleotide sequences of various Wnt proteins from various species are known. See, e.g., Gavin et al. (1990) *Genes Dev.* 4:2319-

2332; Lee et al. (1995) *Proc. Natl. Acad. Sci. USA* 92:2268-2272; and, Christiansen et al. (1995) *Mech. Dev.* 51:341-350 (describing, e.g., murine Wnt1, Wnt2, Wnt3a, Wnt3b, Wnt4, Wnt5a, Wnt 5b, Wnt6, Wnt7a, Wnt7b, Wnt8a, Wnt8b, Wnt10b, Wnt11, Wnt12) and Vant Veer et al. (1984) *Mol. Cell. Biol.* 4:2532-2534; Wainwright et al. (1988) *EMBO J.* 7:1743-1748; and, PCT Publication WO 95/17416 (describing, e.g., human Wnt1, Wnt2, Wnt3, Wnt4, Wnt5a, Wnt7a and Wnt7b).

Analogs of Wnt or Other Proteins Involved in the Wnt-β-Catenin Signaling Pathway Analogs can differ from naturally occurring protein in amino acid sequence or in ways that do not involve sequence, or both. Non-sequence modifications include in vivo or in vitro chemical derivatization of the protein. Non-sequence modifications include changes in acetylation, methylation, phosphorylation, carboxylation, or glycosylation.

Preferred analogs include a protein, e.g., Wnt, (or biologically active fragments thereof) whose sequences differ from the wild-type sequence by one or more conservative amino acid substitutions or by one or more non-conservative amino acid substitutions, deletions, or insertions which do not abolish the biological activity. In a preferred embodiment, the sequence can differ from wild-type sequence by 1, 2, 3, 5, 10, but not more than 20 to 30 amino acid residues. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Production of Fragments and Analogs

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc* 3rd *Cleveland Sympos. Macromolecules*, ed.

AG Walton, Amsterdam: Elsevier pp 273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765-[1978]).

Cassette Mutagenesis

Another method for preparing variants, cassette mutagenesis, is based on the technique described by Wells et al. (*Gene,* 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a Frz receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with Wnt. These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a Wnt molecule or a fragment thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370-1371; and Goward et al. (1992) TIBS 18:136-140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007-16010; Griffiths et al. (1993) EMBO J. 12:725-734; Clackson et al. (1991) Nature 352:624-628; and Barbas et al. (1992) PNAS 89:4457-4461).

A common approach uses the maltose receptor of E. coli (the outer membrane protein, LamB) as a peptide fusion partner (Charbit et al. (1986) EMBO 5, 3029-3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387-392), PhoE (Agterberg, et al. (1990) Gene 88, 37-45), and PAL (Fuchs et al. (1991) Bio/Tech 9, 1369-1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984-993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080-1083). Surface proteins of other bacterial species have also served as peptide fusion partners. Examples include the Staphylococcus protein A and the outer membrane protease IgA of Neisseria (Hansson et al. (1992) J. Bacteriol. 174, 4239-4245 and Klauser et al. (1990) EMBO J. 9, 1991-1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865-1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) Proc. Natl. Acad. Sci. U.S.A. 87, 6378-6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) J. Med. Chem. 37(9):1233-1251). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233-1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204, 357-364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject Wnt polypeptides to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Fusion Proteins

Polypeptides for modulating the level of Wnt protein can be fused to another protein or portion thereof. For example, a Wnt protein or portion thereof, such as the Frizzled binding portion of Wnt, can be operably linked to another polypeptide moiety to enhance solubility. Examples of a protein which can be fused with Wnt or portions thereof include a plasma protein or fragment thereof, which can improve the circulating half life of Wnt. For example, the fusion protein can be a Wnt-immunoglobulin (Ig) fusion protein in which the Wnt sequence is fused to a sequence derived from the immunoglobulin superfamily. Several soluble fusion protein constructs have been disclosed wherein the extracellular domain of a cell surface glycoprotein is fused with the constant F(c) region of an immunoglobulin. For example, Capon et al. (1989) *Nature* 337(9):525-531, provide guidance on generating a longer lasting CD4 analog by fusing CD4 to an immunoglobulin (IgG1). See also, Capon et al., U.S. Pat. Nos. 5,116,964 and 5,428,130 (CD4-IgG fusion constructs); Linsley et al., U.S. Pat. No. 5,434,131 (CTLA4-IgG1 and B7-IgG1 fusion constructs); Linsley et al. (1991) *J. Exp. Med.* 174:561-569 (CTLA4-IgG1 fusion constructs); and Linsley et al. (1991) *J. Exp. Med.* 173:721-730 (CD28-IgG1 and B7-IgG1 fusion constructs). Such fusion proteins have proven useful for modulating receptor-ligand interactions and reducing inflammation in vivo. For example, fusion proteins in which an extracellular domain of cell surface tumor necrosis factor receptor (TNFR) proteins has been fused to an immunoglobulin constant (Fc) region have been used in vivo. See, for example, Moreland et al. (1997) *N. Engl. J. Med.* 337(3):141-147; and, van der Poll et al. (1997) *Blood* 89(10): 3727-3734).

Antibodies

The invention also includes antibodies specifically reactive with a subject Wnt polypeptides or Frizzled as well as antibodies specifically reactive with other proteins of the Wnt-β-catenin signaling pathway, e.g., intrabodies. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

A Wnt protein, or a portion or fragment thereof, can be used as an immunogen to generate antibodies that bind Wnt using standard techniques for polyclonal and monoclonal antibody preparation. The full-length Wnt protein can be used or, alternatively, antigenic peptide fragments of Wnt can be used as immunogens.

Typically, Wnt or a Wnt peptide is used to prepare antibodies by immunizing a suitable subject, (e.g., rabbit, goat, mouse or other mammal) with the immunogen. An appropriate immunogenic preparation can contain, for example, a recombinant Wnt peptide, or a chemically synthesized Wnt peptide. See, e.g., U.S. Pat. No. 5,460,959; and co-pending U.S. applications U.S. Ser. No. 08/334,797; U.S. Ser. No. 08/231,439; U.S. Ser. No. 08/334,455; and U.S. Ser. No. 08/928,881 which are hereby expressly incorporated by reference in their entirety. The nucleotide and amino acid sequences of Wnt are known and described, for example, in Vant Veer et al. (1984) Mol. Cell. Biol. 4:2532-2534, Gavin et al. (1992) *Gene Dev.* 4:2319-2332; Lee et al. (1995) *Proc. Natl. Acad. Sci. USA* 92:2268-2272; Christiansen et al. (1995) Mech. Dev. 51:341-350, Wainwright et al. (1988) EMBO J. 7:1743-1748; and, PCT Publication WO 95/17416. The nucleotide and amino acid sequence of other members of the Wnt-β-catenin signal pathway are also known. The preparation can further include an adjuvant, such as Freund's complete or incomplete adjuvant, or similar immunostimulatory agent. Immunization of a suitable subject with an immunogenic Wnt preparation induces a polyclonal anti-Wnt antibody response.

Anti-Wnt antibodies or fragments thereof can be used to inhibit the levels of Wnt protein. Examples of anti-Wnt antibody fragments include F(v), Fab, Fab' and F(ab')$_2$ fragments which can be generated by treating the antibody with an enzyme such as pepsin. The term "monoclonal antibody" or "monoclonal antibody composition", as used herein, refers to a population of antibody molecules that contain only one species of an antigen binding site capable of immunoreacting with a particular epitope of Wnt. A monoclonal antibody composition thus typically displays a single binding affinity for a particular Wnt protein with which it immunoreacts.

Additionally, anti-Wnt antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., *Science* 240:1041-1043, 1988; Liu et al., *PNAS* 84:3439-3443, 1987; Liu et al., *J. Immunol.* 139:3521-3526, 1987; Sun et al. *PNAS* 84:214-218, 1987; Nishimura et al., *Canc. Res.* 47:999-1005, 1987; Wood et al., *Nature* 314:446-449, 1985; and Shaw et al., *J. Natl. Cancer Inst.* 80:1553-1559, 1988); Morrison, S. L., *Science* 229: 1202-1207, 1985; Oi et al., *BioTechniques* 4:214, 1986; Winter U.S. Pat. No. 5,225,539; Jones et al., *Nature* 321:552-525, 1986; Verhoeyan et al., *Science* 239:1534, 1988; and Beidler et al., *J. Immunol.* 141:4053-4060, 1988.

In addition, a human monoclonal antibody directed against Wnt can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) *Nature* 368: 856-859; Green, L. L. et al. (1994) *Nature Genet.* 7:13-21; Morrison, S. L. et al. (1994) *Proc. Natl. Acad. Sci. USA* 81:6851-6855; Bruggeman et al. (1993) *Year Immunol* 7:33-40; Choi et al. (1993) *Nature Genet.* 4:117-123; Tuaillon et al. (1993) *PNAS* 90:3720-3724; Duchosal et al. PCT publication WO 93/05796; U.S. Pat. No. 5,411,749; McCune et al. (1988) *Science* 241:1632-1639), Kamel-Reid et al. (1988) *Science* 242:1706; Spanopoulou (1994) *Genes & Development* 8:1030-1042; Shinkai et al. (1992) *Cell* 68:855-868). A human antibody-transgenic mouse or an immune deficient mouse engrafted with human antibody-producing cells or tissue can be immunized with Wnt or an antigenic Wnt peptide and splenocytes from these immunized mice can then be used to create hybridomas. Methods of hybridoma production are well known.

Human monoclonal antibodies against Wnt can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) *J. Mol. Biol.* 222:581-597; and Griffths et al. (1993) *EMBO J* 12:725-734. In addition, a combinatorial library of antibody variable regions can be generated by mutating a known human antibody. For example, a variable region of a human antibody known to bind Wnt, can be mutated, by for example using randomly altered mutagenized oligonucleotides, to generate a library of mutated variable regions which can then be screened to bind to Wnt. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) *Proc. Nat'l Acad. Sci. USA* 89:4457-4461.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) supra; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982. Once displayed on the surface of a display package (e.g., filamentous phage), the antibody library is screened to identify and isolate packages that express an antibody that binds Wnt. In a preferred embodiment, the primary screening of the library involves panning with an immobilized Wnt and display packages expressing antibodies that bind immobilized Wnt are selected.

Antisense Wnt Nucleic Acid Sequences

Nucleic acid molecules which are antisense to a nucleotide encoding Wnt can be used as an agent which inhibits Wnt expression. An "antisense" nucleic acid includes a nucleotide sequence which is complementary to a "sense" nucleic acid encoding Wnt, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire Wnt coding strand, or to only a portion thereof. For example, an antisense nucleic acid molecule which antisense to the "coding region" of the coding strand of a nucleotide sequence encoding Wnt can be used.

The coding strand sequences encoding Wnt are known. For example, at least 7 Wnt genes have been identified in human (Wnt-1, 2, 3, 4, 5a, 7a and 7b). See, e.g., Vant Veer et al. (1984) Mol. Cell. Biol. 4:2532-2534, Gavin et al. (1992) *Gene Dev.* 4:2319-2332; Lee et al. (1995) *Proc. Natl. Acad. Sci. USA* 92:2268-2272; Christiansen et al. (1995) Mech. Dev. 51:341-350, Wainwright et al. (1988) EMBO J. 7:1743-1748; and, PCT Publication WO 95/17416. Given the coding strand sequences encoding Wnt, antisense nucleic acids can be designed according to the rules of Watson and Crick base pairing. The antisense nucleic acid molecule can be complementary to the entire coding region of Wnt mRNA, but more preferably is an oligonucleotide which is antisense to only a portion of the coding or noncoding region of Wnt mRNA. For example, the antisense oligonucleotide can be complementary to the region surrounding the translation start site of Wnt mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Gene Therapy

The gene constructs of the invention can also be used as a part of a gene therapy protocol to deliver nucleic acids encoding either an agonistic or antagonistic form of a Wnt polypeptide. The invention features expression vectors for in vivo transfection and expression of a Wnt polypeptide in particular cell types so as to reconstitute the function of, or alternatively, antagonize the function of a Wnt polypeptide in a cell in which that polypeptide is misexpressed. Expression constructs of Wnt polypeptides, may be administered in any biologically effective carrier, e.g. any formulation or composition capable of effectively delivering the Wnt gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a Wnt polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of a Wnt polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Wnt gene by the targeted cell. Exemplary gene delivery systems of this type include liposomal derived systems, poly-lysine conjugates, and artificial viral envelopes.

In a representative embodiment, a gene encoding a Wnt polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075).

In clinical settings, the gene delivery systems for the therapeutic Wnt gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In other preferred embodiments, ex vivo gene therapy approaches can be used.

Cell Therapy

Wnt can also be increased in a subject by introducing into a cell, e.g., a fibroblast, keratinocyte, epithelial cell, e.g., a hair follicle cell, e.g., a DP cell, a nucleotide sequence that modulates the production of Wnt, e.g., a nucleotide sequence encoding a Wnt polypeptide or functional fragment or analog thereof, a promoter sequence, e.g., a promoter sequence from a Wnt gene or from another gene; an enhancer sequence, e.g., 5' untranslated region (UTR), e.g., a 5' UTR from a Wnt gene or from another gene, a 3' UTR, e.g., a 3' UTR from a Wnt gene or from another gene; a polyadenylation site; an insulator sequence; or another sequence that modulates the expression of Wnt. The cell can then be introduced into the subject.

Primary and secondary cells to be genetically engineered can be obtained from a variety of tissues and include cell types which can be maintained propagated in culture. For example, primary and secondary cells include fibroblasts, keratinocytes, epithelial cells (e.g., DP cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient) of the same species or another species (e.g., mouse, rat, rabbit, cat, dog, pig, cow, bird, sheep, goat, horse).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding Wnt, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous Wnt sequence. An exogenous nucleic acid sequence can be introduced into a primary or secondary cell by homologous recombination as described, for example, in U.S. Pat. No. 5,641,670, the contents of which are incorporated herein by reference.

The transfected primary or secondary cells may also include DNA encoding a selectable marker which confers a selectable phenotype upon them, facilitating their identification and isolation. Methods for producing transfected primary and secondary cells which stably express exogenous synthetic DNA, clonal cell strains and heterogeneous cell strains of such transfected cells, methods of producing the clonal heterogeneous cell strains, and methods of treating or preventing an abnormal or undesirable condition through the use of populations of transfected primary or secondary cells are part of the present invention.

Transfection of Primary or Secondary Cells of Clonal or Heterogeneous Cell Strains Vertebrate tissue can be obtained by standard methods such a punch biopsy or other surgical methods of obtaining a tissue source of the primary cell type of interest. For example, punch biopsy or removal of a hair follicle is used to obtain a source of fibroblasts, keratinocytes, or endothelial cells, e.g., hair follicle cells or DP cells. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. The exogenous nucleic acid sequence can optionally include DNA encoding a selectable marker. The exogenous nucleic acid sequence and selectable marker-encoding DNA can either be on separate constructs or on a single construct. An appropriate quantity of DNA is used to ensure that at least one stably transfected cell containing and appropriately expressing exogenous DNA is produced. In general, approximately 0.1 to 500 μg of DNA is used.

As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation.

Electroporation is carried out at approximate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. Total DNA of approximately 0.1 to 500 μg is generally used.

Methods such as calcium phosphate precipitation, modified calcium phosphate precipitation an polybrene precipitation, liposome fusion and receptor-mediated gene delivery can also be used to transect cells. Primary or secondary cells can also be transfected using microinjection. A stably, transfected cell can then be isolated and cultured and sub cultivated, under culturing conditions and for sufficient time to propagate stably transfected secondary cells an produce a clonal cell strain of transfected secondary cells. Alternatively, more than one transfected cell is cultured and sub cultured, resulting in production of a heterogeneous cell strain.

Transfected primary or secondary cells undergo sufficient number doubling to produce either a clonal cell strain or a heterogeneous cell strain of sufficient size to provide the therapeutic protein to an individual in effective amounts. In general, for example, 0.1 $cm^2$ of skin is biopsies and assumed to contain 1,000,000 cells; one cell is used to produce a clonal cell strain and undergoes approximately 27 doublings to produce 100 million transfected secondary cells. If a heterogeneous cell strain is to be produced from an original transfected population of approximately 1000,000 cells, only 10 doublings are needed to produce 100 million transfected cells.

The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. The put these factors in perspective, to deliver therapeutic levels of human growth hormone in an otherwise healthy 10 kg patient with isolated growth hormone deficiency, approximately one to five hundred million transfected fibroblast would be necessary (the volume of these cells is about that of the very tip of the patient's thumb).

Implantation of Clonal Cell Strain or Heterogeneous Cell Strain of Transfected Secondary Cells The transfected cells, e.g., cells produced as described herein, can be introduced into an individual to whom the product is to be delivered. The clonal cell strain or heterogeneous cell strain is then introduced into an individual. Various routed of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from a condition related to unwanted angiogenesis is a candidate for implantation of Wnt producing cells.

The individual can have a small skin biopsy performed; this is a simple procedure which can be performed on an outpatient basis. The piece of skin is taken, for example, from under the arm and can require about one minute to remove. The sample is processed, resulting in isolation of the patient's cell (e.g., fibroblasts) and genetically engineered to produce Wnt or another protein or molecule that induces the production of Wnt. Based on the age, weight, and clinical condition of the patient, the required number of cells are grown in large-scale culture. The entire process should require 4-6 weeks and, at the end of that time, the appropriate number of genetically engineered cells are introduced into the individual, once again as an outpatient (e.g., by injecting them back under the patient's skin, e.g., on the scalp or face). The patient is now capable of producing Wnt which can ameliorate symptoms of hair loss.

For some, this will be a one-time treatment and, for others, multiple cell therapy treatments will be required.

As this example suggests, the cells used will generally be patient-specific genetically engineered cells. It is possible, however, to obtain cells from another individual of the same species or from a different species. Use of such cells might require administration of an immunosuppressant, alteration of histocompatibility antigens, or use of a barrier device to prevent rejection of the implanted cells.

Transfected primary or secondary cells can be administered alone or in conjunction with a barrier or agent for inhibiting immune response against the cell in a recipient subject. For example, an immunosuppressive agent can be administered to a subject to inhibit or interfere with normal response in the subject. Preferably, the immunosuppressive agent is an immunosuppressive drug which inhibits T cell/or B cell activity in a subject. Examples of such immunosuppressive drugs commercially available (e.g., cyclosporin A is commercially available from Sandoz Corp. East Hanover, N.J.).

An immunosuppressive agent, e.g., drug, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) *N. Engl. J. Med.* 327: 1549; Spencer et al. (1992) *N. Engl. J. Med.* 327:1541' Widner et al. (1992) *n. Engl. J. Med.* 327:1556). Dosage values may vary according to factors such as the disease state, age, sex, and weight of the individual.

Another agent with can be used to inhibit T cell activity in a subject is an antibody, or fragment of derivative thereof. Antibodies capable of depleting or sequestering T cells in vivo are known in the art. Polyclonal antisera can be used, for example, anti-lymphocyte serum. Alternatively, one or more monoclonal antibodies can be used. Preferred T cell depleting antibodies include monoclonal antibodies which bind to CD2, CD3, CD4, CD8, CD40, CD40, ligand on the cell surface. Such antibodies are known in the art and are commercially available, for example, from American Type Culture Collection. A preferred antibody for binding CD3 on human T cells is OKT3 (ATCC CRL 8001).

An antibody which depletes, sequesters or inhibits T cells within a recipient subject can be administered in a dose for an appropriate time to inhibit rejection of cells upon transplantation. Antibodies are preferably administered intravenously in a pharmaceutically acceptable carrier of diluent (e.g., saline solution).

An advantage of the use of transfected or secondary cells is that by controlling the number of cells introduced into an individual, one can control the amount of the protein delivered to the body. In addition, in some cases, it is possible to remove the transfected cells of there is no longer a need for the product. A further advantage of treatment by use of transfected primary or secondary cells of the present invention is that production of the therapeutic product can be regulated, such as through the an administration of zinc, steroids or an agent which affects transcription of a protein, product or nucleic acid product or affects the stability of a nucleic acid product.

Administration

An agent which modulates the level of expression of a Wnt protein can be administered to a subject by standard methods. For example, the agent can be administered by any of a number of different routes including intravenous, intradermal, subcutaneous, oral (e.g., inhalation), transdermal (topical), and transmucosal. In one embodiment, the Wnt modulating agent can be administered topically.

The agent which modulates Wnt protein levels, e.g., nucleic acid molecules, Wnt polypeptides, fragments or analogs, Wnt modulators, and anti-Wnt antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Wnt polypeptide or anti-Wnt antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Such transdermal formulations can by applied to the skin to promote or inhibit hair growth.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *PNAS* 91:3054-3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

The agent which modulates the level of Wnt protein can be administered by locally administration, e.g., topical administration. The agent can be applied once or it can be administered continuously, e.g., the agent is administered with sufficient frequency such that the affect on the Wnt protein level is maintained for a selected period, e.g., 5, 10, 20, 30, 50, 90, 180, 365 days or more. The administration of an agent which modulates, e.g., increases or inhibits, the level of a Wnt protein, e.g., a Wnt polypeptide or an anti-Wnt antibody, can also be repeated.

OTHER EMBODIMENTS

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patents and references cited herein are incorporated in their entirety by reference. Other embodiments are within the following claims.

What is claimed:

1. A cell culture comprising: a dermal papilla (DP) cell, a cell culture medium, and an agent that induces Wnt-promoted signal transduction in an amount sufficient to promote or maintain the DP cell in anagen phase, wherein the agent comprises a lithium ion.

2. The cell culture of claim 1, wherein the agent comprises lithium chloride.

3. The cell culture of claim 1, wherein the DP cell is a human DP cell.

4. The cell culture of claim 2, wherein the DP cell is a human DP cell.

5. The cell culture of claim 1, wherein the DP cell is a rodent DP cell.

6. The cell culture of claim 2, wherein the DP cell is a rodent DP cell.

* * * * *

SEQUENCE LISTING

<160> NUMBER OF SEQ ID NOS: 24

<210> SEQ ID NO 1
<211> LENGTH: 17
<212> TYPE: DNA
<213> ORGANISM: Artificial Sequence
<220> FEATURE:
<223> OTHER INFORMATION: Primer for PCR

<400> SEQUENCE: 1
gcgccctggc tcactac                                              17

<210> SEQ ID NO 2

```
<211> LENGTH: 18
<212> TYPE: DNA
<213> ORGANISM: Artificial Sequence
<220> FEATURE:
<223> OTHER INFORMATION: Primer for PCR

<400> SEQUENCE: 2
atgctgctgc tgctggcc                                              18

<210> SEQ ID NO 3
<211> LENGTH: 20
<212> TYPE: DNA
<213> ORGANISM: Artificial Sequence
<220> FEATURE:
<223> OTHER INFORMATION: Primer for PCR

<400> SEQUENCE: 3
tgatccagag gcaggtgcag                                            20

<210> SEQ ID NO 4
<211> LENGTH: 20
<212> TYPE: DNA
<213> ORGANISM: Artificial Sequence
<220> FEATURE:
<223> OTHER INFORMATION: Primer for PCR

<400> SEQUENCE: 4
cttctccagt tctccactgc                                            20

<210> SEQ ID NO 5
<211> LENGTH: 19
<212> TYPE: DNA
<213> ORGANISM: Artificial Sequence
<220> FEATURE:
<223> OTHER INFORMATION: Primer for PCR

<400> SEQUENCE: 5
ctgttgactg caccagctt                                             19

<210> SEQ ID NO 6
<211> LENGTH: 26
<212> TYPE: DNA
<213> ORGANISM: Artificial Sequence
<220> FEATURE:
<223> OTHER INFORMATION: Primer for PCR

<400> SEQUENCE: 6
tcaaggaatg ccagtaccag taccag                                     26

<210> SEQ ID NO 7
<211> LENGTH: 18
<212> TYPE: DNA
<213> ORGANISM: Artificial Sequence
<220> FEATURE:
<223> OTHER INFORMATION: Primer for PCR

<400> SEQUENCE: 7
ctgctagagg accgtgcc                                              18

<210> SEQ ID NO 8
<211> LENGTH: 18
<212> TYPE: DNA
<213> ORGANISM: Artificial Sequence
<220> FEATURE:
<223> OTHER INFORMATION: Primer for PCR

<400> SEQUENCE: 8
```

| | |
|---|---|
| aggtgcgttc ccagtgct | 18 |

```
<210> SEQ ID NO 9
<211> LENGTH: 18
<212> TYPE: DNA
<213> ORGANISM: Artificial Sequence
<220> FEATURE:
<223> OTHER INFORMATION: Primer for PCR

<400> SEQUENCE: 9
```

| | |
|---|---|
| catccttcag cagtgtca | 18 |

```
<210> SEQ ID NO 10
<211> LENGTH: 18
<212> TYPE: DNA
<213> ORGANISM: Artificial Sequence
<220> FEATURE:
<223> OTHER INFORMATION: Primer for PCR

<400> SEQUENCE: 10
```

| | |
|---|---|
| cgtcattgtc attcagag | 18 |

```
<210> SEQ ID NO 11
<211> LENGTH: 18
<212> TYPE: DNA
<213> ORGANISM: Artificial Sequence
<220> FEATURE:
<223> OTHER INFORMATION: Primer for PCR

<400> SEQUENCE: 11
```

| | |
|---|---|
| cagggcacca gagttgat | 18 |

```
<210> SEQ ID NO 12
<211> LENGTH: 18
<212> TYPE: DNA
<213> ORGANISM: Artificial Sequence
<220> FEATURE:
<223> OTHER INFORMATION: Primer for PCR

<400> SEQUENCE: 12
```

| | |
|---|---|
| gcagaagcgg cgttattg | 18 |

```
<210> SEQ ID NO 13
<211> LENGTH: 18
<212> TYPE: DNA
<213> ORGANISM: Artificial Sequence
<220> FEATURE:
<223> OTHER INFORMATION: Primer for PCR

<400> SEQUENCE: 13
```

| | |
|---|---|
| ccaccagcta ggcgcact | 18 |

```
<210> SEQ ID NO 14
<211> LENGTH: 18
<212> TYPE: DNA
<213> ORGANISM: Artificial Sequence
<220> FEATURE:
<223> OTHER INFORMATION: Primer for PCR

<400> SEQUENCE: 14
```

| | |
|---|---|
| gggctcagag ggtccgag | 18 |

```
<210> SEQ ID NO 15
<211> LENGTH: 19
<212> TYPE: DNA
<213> ORGANISM: Artificial Sequence
<220> FEATURE:
```

<223> OTHER INFORMATION: Primer for PCR

<400> SEQUENCE: 15
actgtcaggc gacacttcc                                                      19

<210> SEQ ID NO 16
<211> LENGTH: 18
<212> TYPE: DNA
<213> ORGANISM: Artificial Sequence
<220> FEATURE:
<223> OTHER INFORMATION: Primer for PCR

<400> SEQUENCE: 16
tgcacgttgg gaaggagc                                                       18

<210> SEQ ID NO 17
<211> LENGTH: 18
<212> TYPE: DNA
<213> ORGANISM: Artificial Sequence
<220> FEATURE:
<223> OTHER INFORMATION: Primer for PCR

<400> SEQUENCE: 17
agcctcacag taacaccc                                                       18

<210> SEQ ID NO 18
<211> LENGTH: 18
<212> TYPE: DNA
<213> ORGANISM: Artificial Sequence
<220> FEATURE:
<223> OTHER INFORMATION: Primer for PCR

<400> SEQUENCE: 18
tgttctcctc cagcatga                                                       18

<210> SEQ ID NO 19
<211> LENGTH: 18
<212> TYPE: DNA
<213> ORGANISM: Artificial Sequence
<220> FEATURE:
<223> OTHER INFORMATION: Primer for PCR

<400> SEQUENCE: 19
ttggggatgc tggatggg                                                       18

<210> SEQ ID NO 20
<211> LENGTH: 18
<212> TYPE: DNA
<213> ORGANISM: Artificial Sequence
<220> FEATURE:
<223> OTHER INFORMATION: Primer for PCR

<400> SEQUENCE: 20
cggtcactgg cattgcta                                                       18

<210> SEQ ID NO 21
<211> LENGTH: 19
<212> TYPE: DNA
<213> ORGANISM: Artificial Sequence
<220> FEATURE:
<223> OTHER INFORMATION: Primer for PCR

<400> SEQUENCE: 21
ccacacccgc caccagttc                                                      19

<210> SEQ ID NO 22

```
<211> LENGTH: 18
<212> TYPE: DNA
<213> ORGANISM: Artificial Sequence
<220> FEATURE:
<223> OTHER INFORMATION: Primer for PCR

<400> SEQUENCE: 22
gaggaagagg atgcggca                                                 18

<210> SEQ ID NO 23
<211> LENGTH: 20
<212> TYPE: DNA
<213> ORGANISM: Artificial Sequence
<220> FEATURE:
<223> OTHER INFORMATION: Primer for PCR

<400> SEQUENCE: 23
tgcagtgctt cagccgctac                                               20

<210> SEQ ID NO 24
<211> LENGTH: 20
<212> TYPE: DNA
<213> ORGANISM: Artificial Sequence
<220> FEATURE:
<223> OTHER INFORMATION: Primer for PCR

<400> SEQUENCE: 24
ctcgttgggg tctttgctca                                               20
```